(12) United States Patent
Tsai et al.

(10) Patent No.: US 10,898,261 B2
(45) Date of Patent: Jan. 26, 2021

(54) BIPOLAR ELECTRODE PROBE

(71) Applicant: Industrial Technology Research Institute, Hsinchu (TW)

(72) Inventors: Meng-Han Tsai, Hsinchu County (TW); Hui-Hsin Lu, New Taipei (TW); Wei-Che Lin, Kaohsiung (TW); Ming-Chi Lin, Taichung (TW); Chi-Ying Lu, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 335 days.

(21) Appl. No.: 15/853,856

(22) Filed: Dec. 25, 2017

(65) Prior Publication Data

US 2019/0192216 A1    Jun. 27, 2019

(30) Foreign Application Priority Data

Dec. 22, 2017  (TW) .............................. 106145210 A (51) Int. Cl.
*A61B 18/14* (2006.01)
*A61M 19/00* (2006.01)
(Continued)

(52) U.S. Cl.
CPC ..................... *A61B 18/1477* (2013.01); *A61B 2018/00071* (2013.01); *A61B 2018/00077* (2013.01);
(Continued)

(58) Field of Classification Search
CPC ........... A61B 2018/00071; A61B 2018/00077; A61B 2018/126
See application file for complete search history.

(56) References Cited

U.S. PATENT DOCUMENTS 6,312,428 B1  11/2001  Eggers et al.
6,530,922 B2   3/2003  Cosman et al.
(Continued)

FOREIGN PATENT DOCUMENTS

CN    101022768    8/2007
CN    102860870    1/2013
(Continued)

OTHER PUBLICATIONS

Angelos N. Gazis, et al., "Bipolar radiofrequency ablation of spinal tumors: predictability, safety and outcome," The Spine Journal, vol. 14, No. 4, Apr. 2014, pp. 604-608.
(Continued)

*Primary Examiner* — Ronald Hupczey, Jr.
(74) *Attorney, Agent, or Firm* — JCIPRNET (57) ABSTRACT

Provided is a bipolar electrode probe, which includes a conductive needle, an insulation layer, a conductive sleeve, and an insulation sleeve. The conductive needle has a longitudinal direction and a transverse direction perpendicular to the longitudinal direction. The insulation layer covers the conductive needle and has a first opening. The conductive sleeve covers the insulation layer and has a second opening. The insulation sleeve covers the conductive sleeve. When the bipolar electrode probe is turned on, a longitudinal electric field is formed from a front end of the conductive needle to the conductive sleeve along the longitudinal direction. A transverse electric field is formed from the conductive needle to the conductive sleeve via the first opening and the second opening along the transverse direction.

10 Claims, 8 Drawing Sheets

(51) Int. Cl.
*A61B 18/12* (2006.01)
*A61B 18/00* (2006.01)

(52) U.S. Cl.
CPC .......... *A61B 2018/00083* (2013.01); *A61B 2018/00577* (2013.01); *A61B 2018/126* (2013.01); *A61B 2018/1472* (2013.01); *A61B 2018/1497* (2013.01); *A61B 2218/002* (2013.01)

(56) References Cited

U.S. PATENT DOCUMENTS

| | | | |
|---|---|---|---|
| 7,025,767 | B2 | 4/2006 | Schaefer et al. |
| 7,387,628 | B1 | 6/2008 | Behl et al. |
| 7,416,549 | B2 | 8/2008 | Young et al. |
| 7,976,542 | B1 | 7/2011 | Cosman et al. |
| 8,469,954 | B2 | 6/2013 | Young et al. |
| 8,545,492 | B2 | 10/2013 | Mulier et al. |
| 9,078,665 | B2 | 7/2015 | Moss et al. |
| 9,119,628 | B1 | 9/2015 | Mehta et al. |
| 2004/0193152 | A1* | 9/2004 | Sutton ............ A61B 18/148 606/48 |
| 2005/0228372 | A1* | 10/2005 | Truckai ............ A61B 18/14 606/41 |
| 2005/0288663 | A1 | 12/2005 | Behzadian |
| 2010/0228251 | A1 | 9/2010 | Horlle |
| 2014/0031812 | A1* | 1/2014 | Brannan ............ A61B 18/1815 606/33 |
| 2015/0045675 | A1* | 2/2015 | Chernomorsky ...... A61M 29/02 600/471 |
| 2015/0057658 | A1 | 2/2015 | Sutton et al. |
| 2015/0133916 | A1 | 5/2015 | Shin et al. |
| 2015/0173827 | A1* | 6/2015 | Bloom ............ A61B 18/148 606/39 |
| 2018/0263685 | A1* | 9/2018 | Onik ............ A61B 10/0233 |

FOREIGN PATENT DOCUMENTS

| | | |
|---|---|---|
| CN | 104688333 | 6/2015 |
| JP | 2002507924 | 3/2002 |
| TW | M464141 | 11/2013 |
| WO | 2012153927 | 11/2012 |
| WO | 2016118752 | 7/2016 |

OTHER PUBLICATIONS

C. M. Sommer, et al., "CT-guided Bipolar and Multipolar Radiofrequency Ablation (RF Ablation) of Renal Cell Carcinoma: Specific Technical Aspects and Clinical Results," Cardiovasc Intervent Radiol, vol. 36, No. 3, Aug. 2012, pp. 731-737.

S. G. C. Kroeze, et al., "Clinical efficacy of bipolar radiofrequency ablation of small renal masses," World Journal of Urology, vol. 33, No. 10, Oct. 2014, pp. 1535-1540.

Zhang M, et al., "Efficacy and Safety of Ultrasound-Guided Radiofrequency Ablation for Treating Low-Risk Papillary Thyroid Microcarcinoma: A Prospective Study," Thyroid, vol. 26, No. 11, Nov. 2016, pp. 1-27.

Jin Gy, et al., "Radio Frequency Ablation in the Rabbit Lung Using Wet Electrodes: Comparison of Monopolar and Dual Bipolar Electrode Mode," Korean Journal of Radiology, vol. 7, No. 2, Jun. 2006, pp. 97-105.

Eun Sun Lee, et al., "Evaluation of the in Vivo Efficiency and Safety of Hepatic Radiofrequency Ablation Using a 15-G Octopus® in Pig Liver," Korean Journal of Radiology, vol. 14, No. 2, Mar./Apr. 2013, pp. 194-201.

Mi-Hyun Park, et al., "Comparison of Internally Cooled Wet Electrode and Hepatic Vascular Inflow Occlusion Method for Hepatic Radiofrequency Ablation," Gut and Liver, vol. 6, No. 4, Oct. 2012, pp. 471-475.

Jeong Min Lee, et al., "Wet radio-frequency ablation using multiple electrodes: comparative study of bipolar versus monopolar modes in the bovine liver," European Journal of Radiology, vol. 54, No. 3, Jun. 2005, pp. 408-417.

Y. Korkusuz, et al., "Bipolar Radiofrequency Ablation of Benign Symptomatic Thyroid Nodules: Initial Experience," Rofo. , vol. 188, No. 7, Jul. 2016, pp. 671-675.

Xiao-Long Li, et al., "Treatment efficacy and safety of ultrasound-guided percutaneous bipolar radiofrequency ablation for benign thyroid nodules," British Institute of Radiology, vol. 89, No. 1059, Feb. 2016, pp. 1-8.

Notice of Allowance of Taiwan Counterpart Application, dated Jul. 23, 2018, pp. 1-3.

"Search Report of European Counterpart Application," dated Oct. 9, 2018, pp. 1-8.

"Office Action of Japan Counterpart Application," date Jan. 22, 2019, p. 1-p. 3.

* cited by examiner

BIPOLAR ELECTRODE PROBE

CROSS-REFERENCE TO RELATED APPLICATION

This application claims the priority benefit of Taiwan application serial no. 106145210, filed on Dec. 22, 2017. The entirety of the above-mentioned patent application is hereby incorporated by reference herein and made a part of this specification.

BACKGROUND

Technical Field

The disclosure relates to an electrode probe and more particularly relates to a bipolar electrode probe.

Description of Related Art

In terms of RFA (Radiofrequency Ablation) electrode probes used for clinical purposes, at present unipolar electrode probe is the most commonly used type. However, such a unipolar electrode probe system has a large ablation range and therefore may easily burn the normal superficial skin when used to treat superficial diseases. The unipolar electrode probe system may also put patients having heart disease or carrying pacemakers, pregnant women, and fetuses at risk.

As an attempt to solve the aforementioned problems of the unipolar electrode probe, the bipolar electrode probe has been proposed for clinical uses. Nevertheless, the existing bipolar electrode probe still faces the following problems. First, the bipolar electrode probe is formed by coupling the active electrode, the insulation layer, and the passive electrode, but the mechanical strength may be weak at the junction and the probe may easily break during operation, or the cooling water inside may leak from the junction. Second, for the bipolar electrode probe, the length of the ablation region cannot be adjusted. Generally, the length of the conductive region of the bipolar electrode probe is designed to be about 0.9 cm and thus the bipolar electrode probe cannot be used to ablate a target tissue of 0.9 cm or shorter. Third, for the bipolar electrode probe, it is required to dispose electrically isolated conductive wires and solder joints inside. For this reason, the bipolar electrode probe has a complicated structure and is difficult to manufacture and be made compact.

In view of the above, how to design a bipolar electrode probe that has a simple structure and an adjustable ablation range is an issue that needs to be addressed in this field.

SUMMARY

The disclosure provides a bipolar electrode probe, which includes: a conductive needle, an insulation layer, a conductive sleeve, and an insulation sleeve. The conductive needle has a longitudinal direction and a transverse direction perpendicular to the longitudinal direction. The insulation layer covers the conductive needle and has a first opening. The conductive sleeve covers the insulation layer and has a second opening. The insulation sleeve covers the conductive sleeve. When the bipolar electrode probe is turned on, a longitudinal electric field is formed from a front end of the conductive needle to the conductive sleeve along the longitudinal direction; and a transverse electric field is formed from the conductive needle to the conductive sleeve via the first opening and the second opening along the transverse direction.

To make the aforementioned more comprehensible, several embodiments accompanied with drawings are described in detail as follows.

DESCRIPTION OF THE EMBODIMENTS

Figure 1:
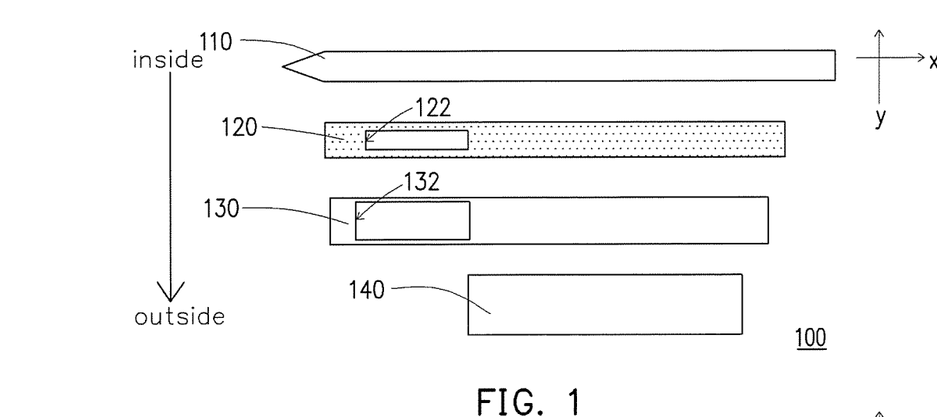
FIG. 1 is a schematic view of an exploded state of the bipolar electrode probe according to an embodiment of the disclosure.
Figure 2:
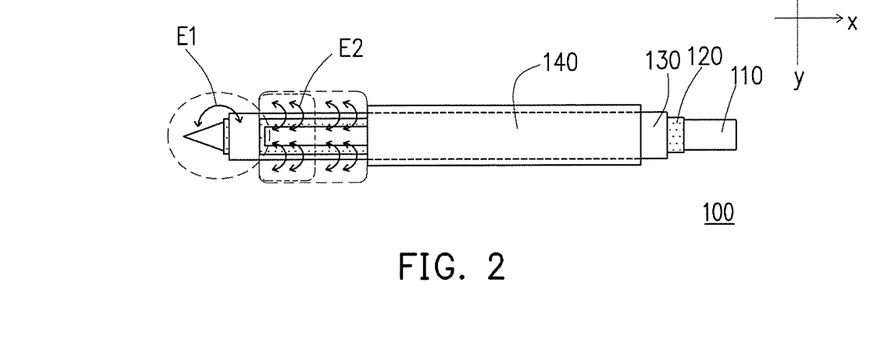
FIG. 2 is a schematic view of a combined state of the bipolar electrode probe according to an embodiment of the disclosure.

FIG. 1 is a schematic view of an exploded state of a bipolar electrode probe according to an embodiment of the disclosure. FIG. 2 is a schematic view of a combined state of the bipolar electrode probe according to an embodiment of the disclosure. Referring to FIG. 1 and FIG. 2, the bipolar electrode probe 100 includes: a conductive needle 110, an insulation layer 120, a conductive sleeve 130, and an insulation sleeve 140 from the inside to the outside. Embodiments of the bipolar electrode probe 100 and embodiments of each component will be described hereinafter.

The conductive needle 110 has a longitudinal direction x and a transverse direction y perpendicular to the longitudinal direction x. The insulation layer 120 covers the conductive needle 110 and has a first opening 122. The conductive sleeve 130 covers the insulation layer 120 and has a second opening 132. The insulation sleeve 140 covers the conductive sleeve 130. When the bipolar electrode probe 100 is turned on, a longitudinal electric field E1 is formed from a front end of the conductive needle 110 to the conductive sleeve 130 along the longitudinal direction x. A transverse electric field E2 is formed from the conductive needle 110 to the conductive sleeve 130 via the first opening 122 and the second opening 132 along the transverse direction y. In another embodiment, the insulation sleeve 140 is movable along the longitudinal direction x, so as to adjust an ablation range of the bipolar electrode probe 100 (which will be described later).

It should be noted that, in the region where the transverse electric field E2 is generated, a small longitudinal electric field may be formed from the conductive needle 110 to the conductive sleeve 130 via the first opening 122 and the second opening 132 along the longitudinal direction x, but the influence thereof may be ignored and thus is not discussed here. Moreover, in an embodiment, the conductive needle 110 serves as an active electrode while the conductive sleeve 130 serves as a passive electrode, for example, but the disclosure is not limited thereto. In other embodiments, the conductive needle 110 may serve as the passive electrode and the conductive sleeve 130 may serve as the active electrode.

Referring to FIG. 2, the bipolar electrode probe 100 has a front ablation region and a rear ablation region. Specifically, the longitudinal electric field E1 at the front is for ablating a front section of the target tissue, and the transverse electric field E2 at the rear is for ablating a rear section of the target tissue. An embodiment of the structure of the bipolar electrode probe 100 will be described hereinafter.

Figure 3A:
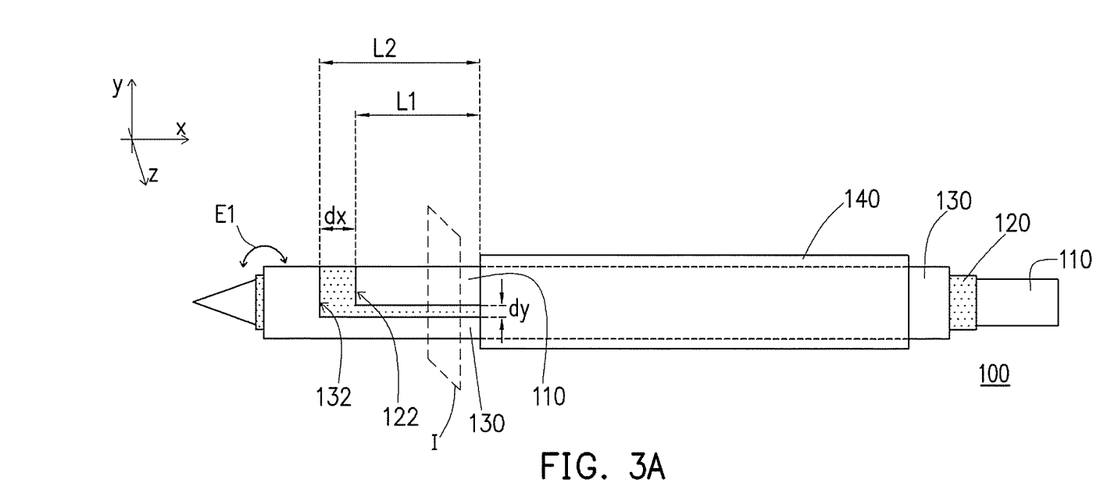
FIG. 3A is a schematic view of the bipolar electrode probe according to an embodiment of the disclosure.
Figure 3B:
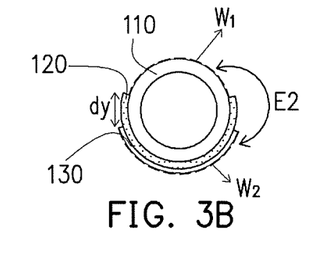
FIG. 3B is a schematic cross-sectional view taken along the plane I of FIG. 3A.

FIG. 3A is a schematic view of the bipolar electrode probe according to an embodiment of the disclosure. FIG. 3A shows the longitudinal direction x, the transverse direction y, and a direction z perpendicular to the longitudinal direction x and the transverse direction y. FIG. 3B is a schematic cross-sectional view taken along the plane I of FIG. 3A. Referring to FIG. 1 and FIG. 3A, the area of the first opening 122 is smaller than the area of the second opening 132, such that a portion of the insulation layer 120 is exposed by the second opening 132, and the exposed region of the insulation layer 120 has a longitudinal insulation distance dx and a transverse insulation distance dy.

Referring to FIG. 2, FIG. 3A, and FIG. 3B, in an embodiment, in the region of the transverse electric field E2, the longitudinal insulation distance dx is from a front end of the second opening 132 to a front end of the first opening 122 along the longitudinal direction x. The transverse insulation distance dy is from one end of the second opening 132 to one end of the first opening 122 on the same side along the transverse direction y. The longitudinal insulation distance dx is to ensure the longitudinal isolation distance between the conductive needle 110 and the conductive sleeve 130, so as to prevent a large current from flowing through the tissue due to a short isolation distance. If the isolation distance between the conductive needle 110 and the conductive sleeve 130 is too short, a large current may flow through the tissue to cause the temperature to rise too quickly and result in coking in a short time, and the ablation range will be only about 0.5 mm of the probe surface. Such a small ablation range is inadequate for clinical use.

In addition, as shown in FIG. 3B, the transverse insulation distance dy ensures the transverse isolation distance between the conductive needle 110 and the conductive sleeve 130, so as to maintain a current path that is sufficient for generating the transverse electric field E2 and prevent reduction of the ablation range due to a short current path.

Referring to FIG. 3A and FIG. 3B, in an embodiment, in the region of the transverse electric field E2, a ratio of the area of the conductive needle 110 exposed by the first opening 122 to the area of the conductive sleeve 130 in the region outside the second opening 132 is 1:0.9 to 1:1.1.

Referring to FIG. 3A and FIG. 3B, in the region of the transverse electric field E2, the area of the conductive needle 110 is L1×W1, wherein L1 is a length of the conductive needle 110 along the longitudinal direction x and W is a length of the conductive needle 110 in a circumferential direction; moreover, the area of the conductive sleeve 130 is L2×W2, wherein L2 is a length of the conductive sleeve 130 along the longitudinal direction x and W2 is a length of the conductive sleeve 130 in the circumferential direction. In an embodiment, the area of the conductive needle 110 may be equal to the area of the conductive sleeve 130, so as to generate the transverse electric field E2 uniformly. In other embodiments, when the ratio of the area of the conductive needle 110 to the area of the conductive sleeve 130 in the region of the transverse electric field E2 is set to 1:0.9 to 1:1.1, the transverse electric field E2 may be generated uniformly.

In addition, referring to FIG. 3A and FIG. 3B, in an embodiment, a ratio of the area of a conductive region where the longitudinal electric field E1 exists to the area of a conductive region where the transverse electric field E2 exists is 1:2.1 to 1:2.6. Thereby, the front ablation region (the longitudinal electric field E1) and the rear ablation region (the transverse electric field E2) of the bipolar electrode probe 100 may be set to a proper ratio.

Further, referring to FIG. 3A and FIG. 3B, in the region of the transverse electric field E2, the longitudinal insulation distance dx and the transverse insulation distance dy define an insulation area, and the area of the conductive needle 110 exposed by the first opening 122 and the area of the conductive sleeve 130 outside the second opening 132 define a conductive area, and a ratio of the insulation area to the conductive area is 1:8 to 1:44.

As shown in FIG. 3A and FIG. 3B, in the region of the transverse electric field E2, the insulation area is the area of the insulation layer 120 that exists in the region of the longitudinal insulation distance dx and the transverse insulation distance dy. In the region of the transverse electric field E2, the conductive area is a sum of the area L1×W1 of the conductive needle 110 and the area L2×W2 of the conductive sleeve 130. Through calculation, it is obtained that the ratio of the insulation area to the conductive area is 1:8 to 1:44. With this setting, the transverse electric field E2 is generated uniformly, so as to perform uniform ablation.

Figure 4A:
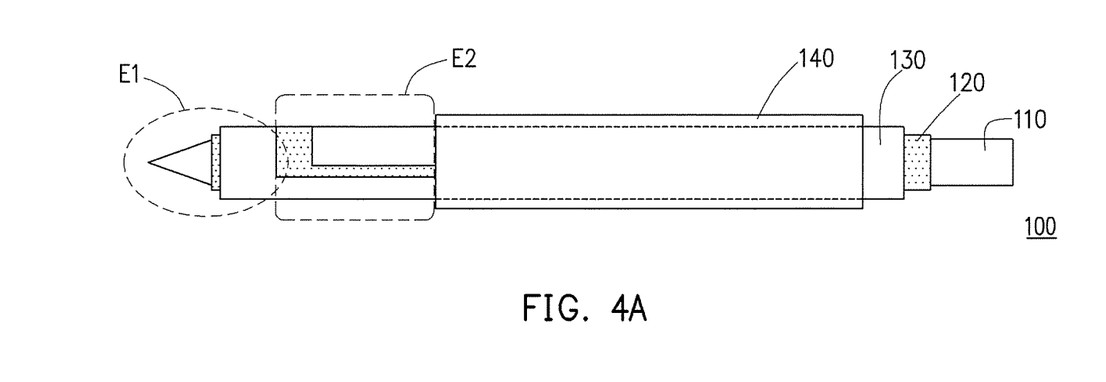
FIG. 4A and FIG. 4B are schematic views showing that the insulation sleeve moves back and forth along the longitudinal direction according to another embodiment of the disclosure.
Figure 4B:
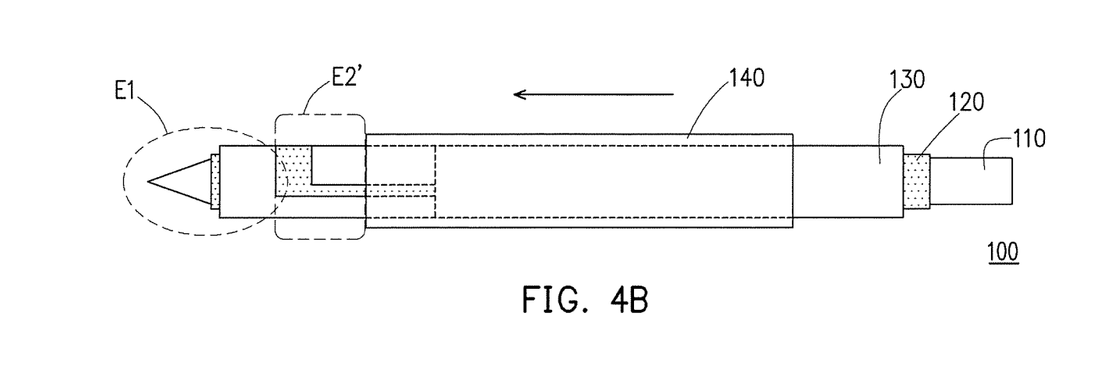

FIG. 4A and FIG. 4B are schematic views showing that the insulation sleeve moves back and forth along the longitudinal direction according to another embodiment of the disclosure. Referring to FIG. 4A and FIG. 4B, relative to the conductive needle 110, the insulation layer 120, and the conductive sleeve 130 disposed at fixed locations, the insulation sleeve 140 is configured to be movable back and forth along the longitudinal direction x. As shown in FIG. 4A and FIG. 4B, when the insulation sleeve 140 moves toward the front end of the bipolar electrode probe 100, the larger transverse electric field E2 changes to a smaller transverse electric field E2'.

In other words, the range of the transverse electric field E2 (ablation region) may be adjusted by moving the insulation sleeve 140 back and forth along the longitudinal direction x. When ablating a superficial tissue of the epidermis, the insulation sleeve 140 may be moved to completely close the transverse electric field E2 and to only use the longitudinal electric field E1 for ablation, so as to prevent burning the epidermis of the patient. In addition, when the insulation sleeve 140 is moved toward the front end of the bipolar electrode probe 100, the range of the transverse electric field E2 is reduced to achieve a smaller ablation region; on the other hand, when the insulation sleeve 140 is moved toward the rear end of the bipolar electrode probe 100, the range of the transverse electric field E2 is increased to achieve a larger ablation region.

In the disclosure, even if the insulation sleeve 140 moves back and forth in the longitudinal direction x, the strength of the transverse electric field E2 in the transverse direction y remains uniform. Therefore, the ablation region is maintained uniform in the transverse direction y.

In the embodiments of FIG. 1 to FIG. 4B, the number of the first openings 122 may be equal to the number of the second openings 132. The number of the first openings 122 is one or more, and the number of the second openings 132 is one or more. Thereby, an electrode pair is formed (as shown in FIG. 3B). In other embodiments, however, the number of the first openings 122 and the number of the second openings 132 may be two, three, four, five, six, and so on, respectively.

Figure 5:
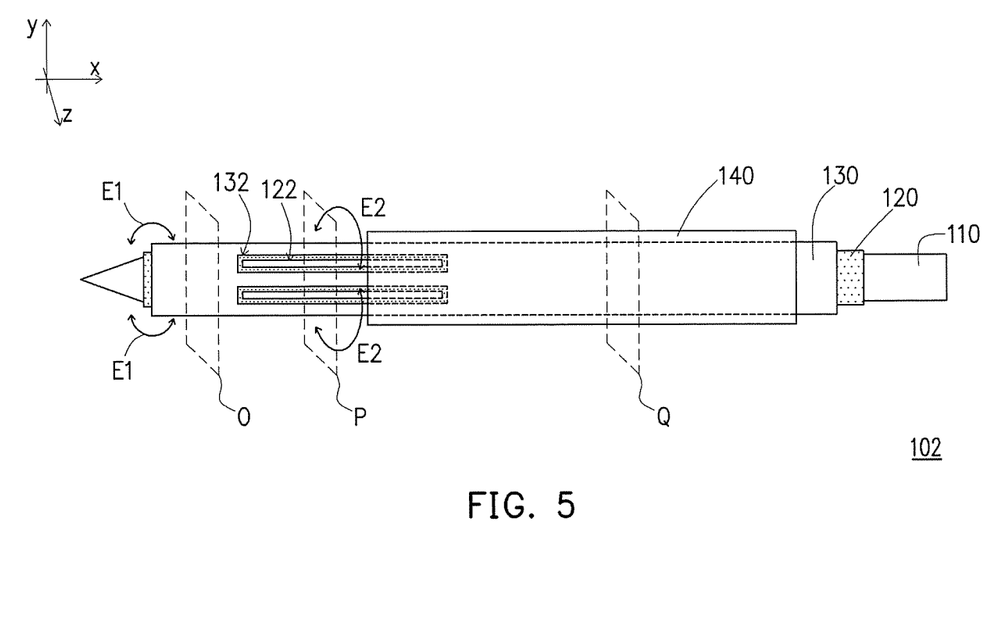
FIG. 5 is a schematic view of the bipolar electrode probe according to another embodiment of the disclosure.
Figure 6A:
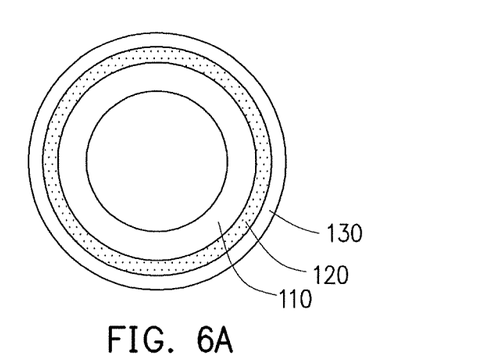
FIG. 6A is a schematic cross-sectional view taken along the plane O of FIG. 5.
Figure 6B:
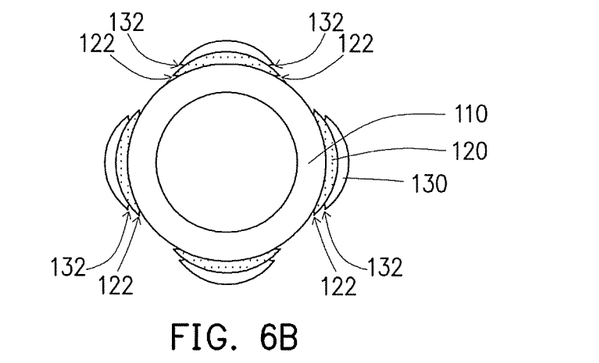
FIG. 6B is a schematic cross-sectional view taken along the plane P of FIG. 5.
Figure 6C:
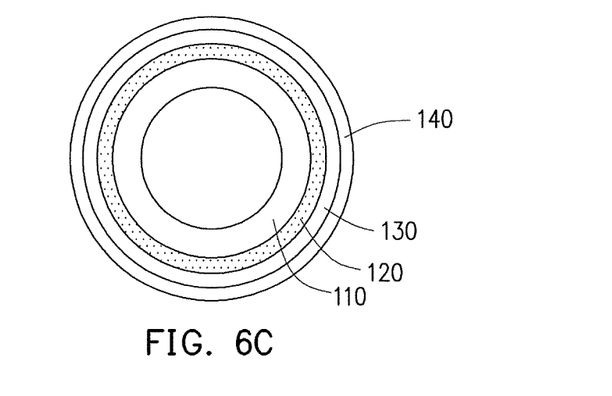
FIG. 6C is a schematic cross-sectional view taken along the plane Q of FIG. 5.

FIG. 5 is a schematic view of the bipolar electrode probe according to another embodiment of the disclosure. FIG. 6A is a schematic cross-sectional view taken along the plane O of FIG. 5. FIG. 6B is a schematic cross-sectional view taken along the plane P of FIG. 5. FIG. 6C is a schematic cross-sectional view taken along the plane Q of FIG. 5. In a bipolar electrode probe 102, identical components are represented by identical reference numerals as shown in FIG. 1 to FIG. 4B, and therefore detailed descriptions thereof are not repeated hereinafter. Referring to FIG. 5 and FIG. 6B, in this embodiment, the number of the first openings 122 is four and the number of the second openings 132 is four, so as to form four electrode pairs (as shown in FIG. 6B).

Figure 7:
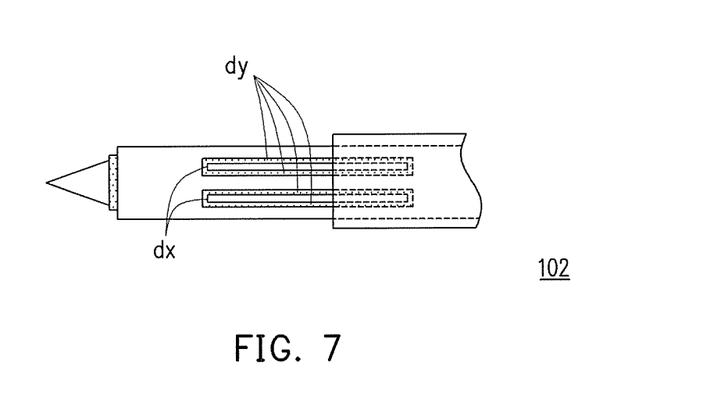
FIG. 7 is a partially enlarged view of the bipolar electrode probe of FIG. 5.

FIG. 7 is a partially enlarged view of the bipolar electrode probe of FIG. 5. Referring to FIG. 7, similarly, in the bipolar electrode probe 102, the region exposed by the insulation layer 120 has the longitudinal insulation distance dx and the transverse insulation distance dy. The longitudinal insulation distance dx is to ensure the longitudinal isolation distance between the conductive needle 110 and the conductive sleeve 130 in the longitudinal direction, so as to prevent a large current from flowing through the tissue due to a short isolation distance. In addition, the transverse insulation distance dy is maintained to ensure the transverse isolation distance between the conductive needle 110 and the conductive sleeve 130, so as to maintain a current path that is sufficient for generating the transverse electric field E2 and prevent reduction of the ablation range due to a short current path.

Figure 8:
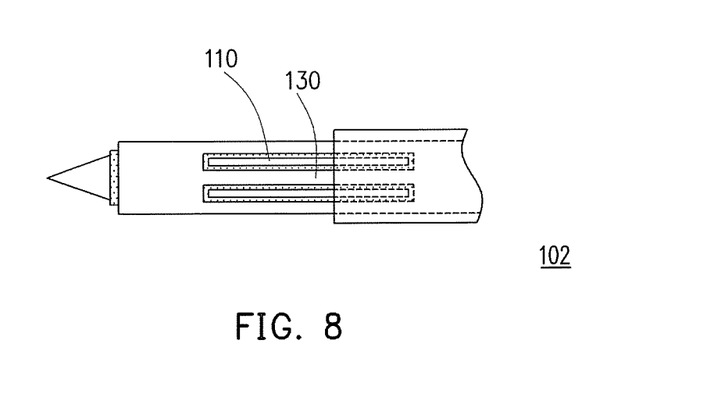
FIG. 8 is a partially enlarged view of the bipolar electrode probe of FIG. 5.

FIG. 8 is a partially enlarged view of the bipolar electrode probe of FIG. 5. Similar to the description of FIG. 3B, as shown in FIG. 8, in the region of the transverse electric field E2, the area of the conductive needle 110 may be equal to the area of the conductive sleeve 130, so as to generate the transverse electric field E2 uniformly. In another embodiment, when the ratio of the area of the conductive needle 110 to the area of the conductive sleeve 130 is set to 1:0.9 to 1:1.1, the transverse electric field E2 may be generated uniformly.

Figure 9:
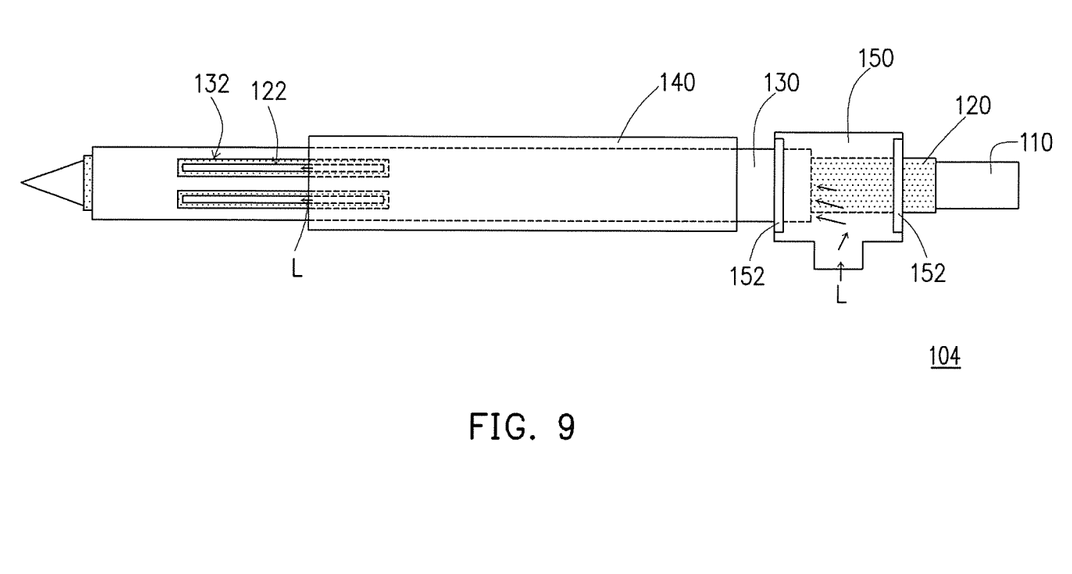
FIG. 9 is a schematic view of the bipolar electrode probe according to another embodiment of the disclosure.

FIG. 9 is a schematic view of the bipolar electrode probe according to another embodiment of the disclosure. Components identical to those in the above embodiments of FIG. 1 to FIG. 8 are represented by identical reference numerals, and therefore detailed descriptions thereof are not repeated hereinafter. Referring to FIG. 9, a bipolar electrode probe 104 of this embodiment may further include: an infusion member 150 disposed at the rear ends of the insulation layer 120 and the conductive sleeve 130. The infusion member 150 is disposed to allow a liquid substance L to pass through a gap between the insulation layer 120 and the conductive sleeve 130 to be outputted from the first opening 122 and the second opening 132.

Referring to FIG. 9, the liquid substance L enters the gap between the insulation layer 120 and the conductive sleeve 130 in the direction indicated by the arrow and flows out from the first opening 122 and the second opening 132 at the front to be infused into the target tissue. In an embodiment, the liquid substance L may be: an anesthetic drug for easing pain in the ablation region or physiological saline for increasing the volume of ablation. When the bipolar electrode probe 104 is used for ablation on an air-related organ (e.g., lungs), infusion of physiological saline facilitates the ablation and solves the problem of poor ablation effect resulting from the fact that gas cannot effectively transfer current and heat.

The infusion member 150 may further include sealing members 152 disposed at a junction between the infusion member 150 and the insulation layer 120 and a junction between the infusion member 150 and the conductive sleeve 130, so as to properly assemble the infusion member 150 to the bipolar electrode probe 104 and enable the liquid substance L to be properly inputted into the inlet of the infusion member 150, and then through the gap between the insulation layer 120 and the conductive sleeve 130, to be outputted to the target tissue from the first opening 122 and the second opening 132.

As shown in FIG. 9, the infusion member 150 is assembled to the bipolar electrode probe 104 that has four first openings 122 and four second openings 132; however, the infusion member 150 may also be assembled to the bipolar electrode probe 100 that has one first opening 122 and one second opening 132, as shown in FIG. 3A.

Figure 10:
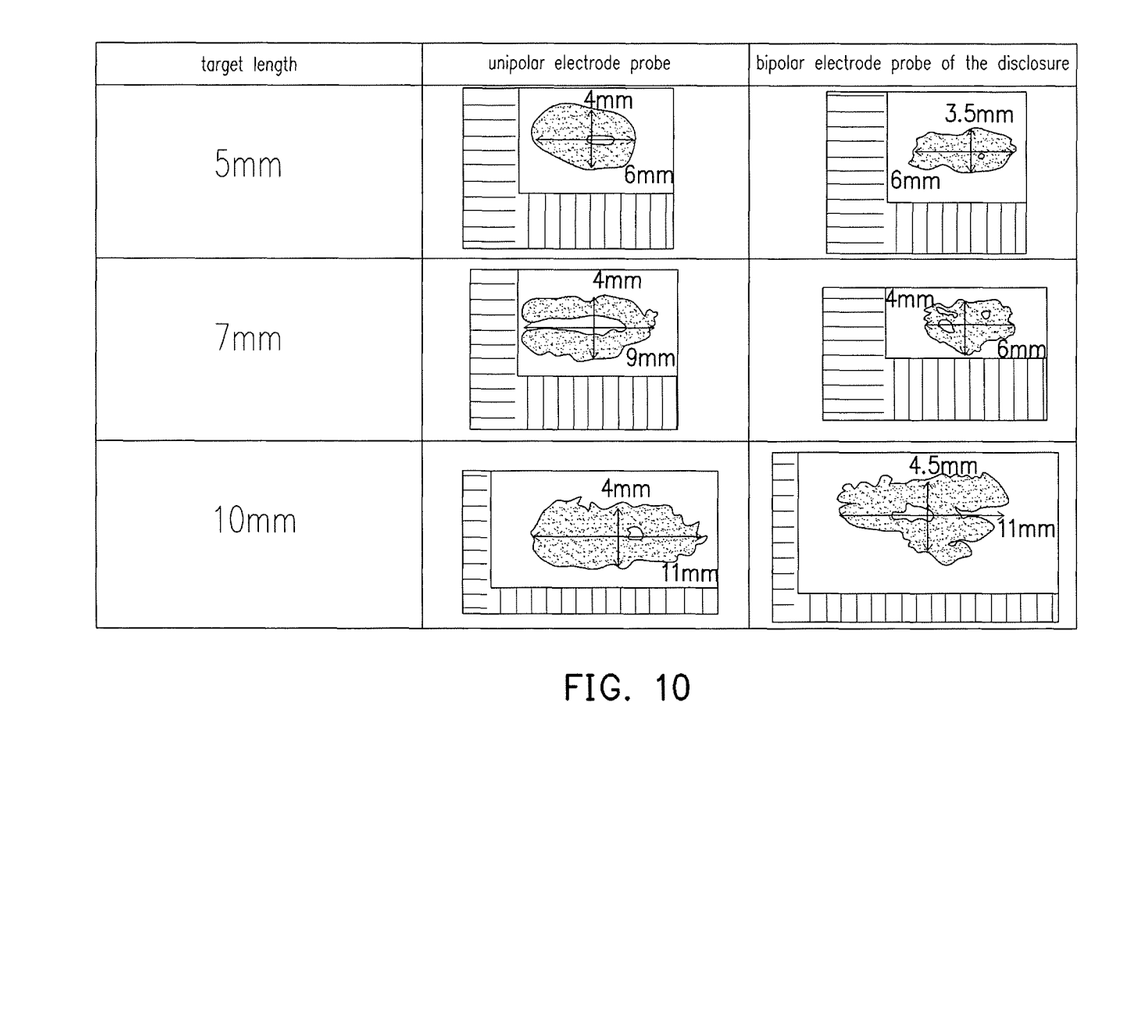
FIG. 10 is a table of comparison between the bipolar electrode probe of FIG. 1 to FIG. 4B and the conventional unipolar electrode probe used for ablating the target tissue.

FIG. 10 is a table of comparison between the bipolar electrode probe of FIG. 1 to FIG. 4B and the conventional unipolar electrode probe used for ablating the target tissue. Referring to FIG. 10, when a target length for ablation of the target tissue is 5 mm, it is known that the unipolar electrode probe forms an ablation region of 6 mm in the longitudinal direction and an ablation region of 4 mm in the transverse direction; on the other hand, the bipolar electrode probe 100 according to the embodiments of the disclosure forms an ablation region of 6 mm in the longitudinal direction and an ablation region of 3.5 mm in the transverse direction, which at least achieves an ablation effect similar to the unipolar electrode probe.

Referring to FIG. 10 again, when the target length for ablation of the target tissue is 7 mm, it is known that the unipolar electrode probe forms an ablation region of 9 mm in the longitudinal direction and an ablation region of 4 mm in the transverse direction; on the other hand, the bipolar electrode probe 100 according to the embodiments of the disclosure forms an ablation region of 6 mm in the longitudinal direction and an ablation region of 4 mm in the transverse direction, which at least achieves an ablation effect similar to the unipolar electrode probe. It is known from the above that the length of the ablation region formed by the unipolar electrode probe in the longitudinal direction is 9 mm, which exceeds the target length 7 mm and the operation accuracy drops. However, the length of the ablation region formed by the bipolar electrode probe 100 of the disclosure in the longitudinal direction is 6 mm, which is close to the target length 7 mm and achieves favorable operation accuracy.

Referring to FIG. 10 again, when the target length for ablation of the target tissue is 10 mm, it is known that the unipolar electrode probe forms an ablation region of 11 mm in the longitudinal direction and an ablation region of 4 mm in the transverse direction; on the other hand, the bipolar electrode probe 100 according to the embodiments of the disclosure forms an ablation region of 11 mm in the longitudinal direction and an ablation region of 4.5 mm in the transverse direction, which at least achieves an ablation effect similar to the unipolar electrode probe.

To sum up, the bipolar electrode probe of the disclosure at least achieves the following. First, the active electrode and the passive electrode are formed on the same needle without use of the conventional additional electrode plate, which prevents an unnecessary current from flowing through the normal organs and improves the safety for patients. Second, the ablation region is formed uniformly, which avoids generating a hot spot and prevents burning the patient's epidermis when ablating a superficial tissue of the epidermis. Third, the bipolar electrode probe has a sleeve-type structure design, which simplifies the overall assembly and avoids weakening the mechanical strength. Furthermore, when the insulation sleeve is configured movable, the insulation sleeve may be moved back and forth along the longitudinal direction, which makes it easy to adjust the range of the transverse electric field (the ablation region) for ablating target tissues of different sizes (e.g., cancer cells) in one operation. Because of the structure design of the disclosure, the transverse electric field has a uniform strength, and when the insulation sleeve is moved along the longitudinal direction to obtain different lengths of conductivity, the target tissue is uniformly heated around the transverse electric field. In addition, when the infusion member is used, the bipolar electrode probe has a channel for injecting liquid substances (e.g., anesthetic) for easing the patient's pain during treatment.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A bipolar electrode probe, comprising:
    a conductive needle having a longitudinal direction and a transverse direction perpendicular to the longitudinal direction;
    an insulation layer covering the conductive needle and having at least a first opening, wherein the insulation layer exposes a needle end portion of the conductive needle;
    a conductive sleeve covering the insulation layer and having at least a second opening; and
    an insulation sleeve covering the conductive sleeve,
    wherein when the bipolar electrode probe is in operation,
        a longitudinal electric field is from the needle end portion of the conductive needle to the conductive sleeve along the longitudinal direction, and
        a transverse electric field is formed from the conductive needle to the conductive sleeve via the at least one first opening and the at least one second opening along the transverse direction.

2. The bipolar electrode probe according to claim 1, wherein
    an area of the at least one first opening is smaller than an area of the at least one second opening.

3. The bipolar electrode probe according to claim 1, wherein
    in a region of the transverse electric field, a longitudinal insulation distance exists between a front end of the at least one second opening and a front end of the at least one first opening along the longitudinal direction; and
    a transverse insulation distance exists between an end of the at least one second opening and an end of the at least one first opening on a same side along the transverse direction.

4. The bipolar electrode probe according to claim 1, wherein
    in a region of the transverse electric field, a ratio of an area of the conductive needle exposed by the at least one first opening to an area of the conductive sleeve in a region outside the at least one second opening is 1:0.9 to 1:1.1,
    wherein the region of the transverse electric field is an area of the conductive sleeve bounded by a front end of the at least one second opening and a rear end of the at least one second opening which is exposed along the longitudinal direction.

5. The bipolar electrode probe according to claim 1, wherein
    a ratio of a first area of a conductive region where the longitudinal electric field exists to a second area of a conductive region where the transverse electric field exists is 1:2.1 to 1:2.6,
    wherein the first area of the conductive region of the conductive needle is defined from a tip of the conductive needle to a front side of the at least one second opening along the longitudinal direction,
    wherein the second area of the conductive region of the conductive needle is defined by a sum of a region of the conductive needle exposed by the at least first opening and a region of the conductive sleeve outside the at least one second opening and exposed by the insulation sleeve and other than the first area.

6. The bipolar electrode probe according to claim 1, wherein
    in a region of the transverse electric field, a longitudinal insulation distance exists between a front end of the at least one second opening and a front end of the at least one first opening along the longitudinal direction; and
    a transverse insulation distance exists between an end of the at least one second opening and an end of the at least one first opening on a same side along the transverse direction,
    wherein the region of the transverse electric field is an area of the conductive sleeve bounded by the front end of the at least one second opening and a rear end of the at least one second opening which is exposed along the longitudinal direction, wherein in the region of the transverse electric field, the longitudinal insulation distance and the transverse insulation distance define an insulation area, and an area of the conductive needle exposed by the at least one first opening and an area of the conductive sleeve outside the at least one second opening define a conductive area, and
    a ratio of the insulation area to the conductive area is 1:8 to 1:44.

7. The bipolar electrode probe according to claim 1, wherein
    the insulation sleeve is movable back and forth along the longitudinal direction.

8. The bipolar electrode probe according to claim 1, wherein
    the number of the at least one first opening is equal to the number of the at least one second opening.

9. The bipolar electrode probe according to claim 1, further comprising:
an infusion member disposed at rear ends of the insulation layer and the conductive sleeve,
wherein the infusion member is configured to allow a liquid substance to pass through a gap between the insulation layer and the conductive sleeve to be outputted from the at least one first opening and the at least one second opening.

10. The bipolar electrode probe according to claim 9, wherein
the infusion member further comprises a plurality of sealing members disposed at a junction between the infusion member and the insulation layer and at a junction between the infusion member and the conductive sleeve.

* * * * *